United States Patent
Allen et al.

(10) Patent No.: US 11,104,941 B2
(45) Date of Patent: Aug. 31, 2021

(54) 5' ADAPTER COMPRISING AN INTERNAL 5'-5' LINKAGE

(71) Applicant: Bioo Scientific Corporation, Austin, TX (US)

(72) Inventors: Kevin Allen, Austin, TX (US); Suk Ho Eun, Austin, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 307 days.

(21) Appl. No.: 16/145,908

(22) Filed: Sep. 28, 2018

(65) Prior Publication Data

US 2020/0102607 A1    Apr. 2, 2020

(51) Int. Cl.
| | | |
|---|---|---|
| *C12Q 1/6855* | (2018.01) | |
| *C12Q 1/6876* | (2018.01) | |
| *C12Q 1/686* | (2018.01) | |
| *C12Q 1/6806* | (2018.01) | |

(52) U.S. Cl.
CPC ......... *C12Q 1/6855* (2013.01); *C12Q 1/6806* (2013.01); *C12Q 1/686* (2013.01); *C12Q 1/6876* (2013.01)

(58) Field of Classification Search
CPC .............................. C12Q 1/6855; C12Q 1/6806
See application file for complete search history.

(56) References Cited

U.S. PATENT DOCUMENTS

| | | | |
|---|---|---|---|
| 5,527,899 A * | 6/1996 | Froehler | C12Q 1/6839 536/25.3 |
| 6,420,546 B1 | 7/2002 | Seliger et al. | |
| 2006/0068433 A1 * | 3/2006 | Godfrey | C12Q 1/686 435/6.18 |
| 2009/0318676 A1 | 12/2009 | Manoharan et al. | |
| 2014/0357528 A1 | 12/2014 | Robb et al. | |
| 2016/0376591 A1 | 12/2016 | Manoharan et al. | |
| 2017/0137875 A1 | 5/2017 | Toloue et al. | |
| 2018/0066311 A1 | 3/2018 | Kazakov | |
| 2018/0195061 A1 | 7/2018 | Schildkraut et al. | |
| 2018/0221494 A1 | 8/2018 | Manoharan et al. | |

FOREIGN PATENT DOCUMENTS

| | | | |
|---|---|---|---|
| WO | WO2000/040592 A1 | 7/2000 | |
| WO | WO-2013096839 A1 * | 6/2013 | ......... C12N 15/1093 |

OTHER PUBLICATIONS

Van de Sande, Parallel Stranded DNA, Science, 241(4865): 551-557, 1988. (Year: 1988).*
Barberán-Soler et al., "Decreasing miRNA sequencing bias using a single adapter and circularization approach", Genome Biology, 2018, 19:105, https://doi.org/10.1186/s13059-018-1488-z.
Fuchs et al., "Bias in Ligation-Based Small RNA Sequencing Library Construction Is Determined by Adaptor and RNA Structure", PLoS ONE, 2015, 10(5): e0126049, doi:10.1371/journal.pone.0126049.
Jackson et al., "Evaluating bias-reducing protocols for RNA sequencing library preparation", BMC Genomics, 2014, 15:569.
Zhuang et al., "Structural bias in T4 RNA ligase-mediated 3'-adapter ligation", Nucleic Acids Research, 2012, 40(7): e54, doi:10.1093/nar/gkr1263.

* cited by examiner

*Primary Examiner* — Samuel C Woolwine
*Assistant Examiner* — Carolyn L Greene
(74) *Attorney, Agent, or Firm* — James S. Keddie; Bozicevic, Field & Francis LLP

(57) ABSTRACT

This disclosure provides, among other things, a 5' adapter of the formula 3'*—X—(5'5')—Y—3', where: 3'* is a blocked 3' end, X is a synthetic sequence, (5'5') is an internal 5'-5' linkage, Y is an adapter sequence, and 3' is a hydroxylated 3' end. In use, sequence X hybridizes to sequence X' in a population of RNA molecules of formula R—X', which increases the efficiency of ligation of the 5' adapter to the nucleic acid molecules.

21 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 17
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (16)..(16)
<223> OTHER INFORMATION: V is G, A or C
```

-continued

```
<220> FEATURE:
<221> NAME/KEY: misc_feature
<222> LOCATION: (17)..(17)
<223> OTHER INFORMATION: n is a, c, g, or t

<400> SEQUENCE: 1
tttttttttt tttttvn                                                    17

<210> SEQ ID NO 2
<211> LENGTH: 30
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (27)..(30)
<223> OTHER INFORMATION: n is a, c, g, or u

<400> SEQUENCE: 2
guucagaguu cuacaguccg acgaucnnnn                                      30

<210> SEQ ID NO 3
<211> LENGTH: 38
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (2)..(2)
<223> OTHER INFORMATION: v is G, A or C
<220> FEATURE:
<221> NAME/KEY: misc_feature
<222> LOCATION: (35)..(38)
<223> OTHER INFORMATION: n is a, c, g, t or u

<400> SEQUENCE: 3 nvtttttgu ucagaguucu acaguccgac gaucnnnn                              38

<210> SEQ ID NO 4
<211> LENGTH: 42
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (2)..(2)
<223> OTHER INFORMATION: v is a, c or g
<220> FEATURE:
<221> NAME/KEY: misc_feature
<222> LOCATION: (39)..(42)
<223> OTHER INFORMATION: n is a, c, g, t or u

<400> SEQUENCE: 4 nvttttttt ttguucagag uucuacaguc cgacgaucnn nn                         42
```

5' ADAPTER COMPRISING AN INTERNAL 5'-5' LINKAGE

BACKGROUND

Many RNA-seq workflows involve a 5' ligation step in which the 3' end of an RNA adapter is ligated onto the 5' end of an RNA molecule (e.g., a fragment of mRNA or a small RNA, for example). This ligation step is not efficient and is known to introduce pronounced bias, such that a given RNA species may be over- or under-represented in the resultant cDNA library by as much as several hundred-fold. Increasing the efficiency and reducing bias in 5' adapter ligation is desirable because, among other things, it would reduce sequencing costs by allowing a greater number of RNAs to be identified at a shallower sequencing depth.

In theory, this problem could be solved using 3' and 5' adapters that have complementary regions. In this method, ligation of the 3' adapter to an RNA molecule followed by addition of the 5' adapter would bring the 5' adapter into proximity with the 5' end of the RNA, thereby facilitating ligation of the 5' adapter and reducing bias introduced during 5' ligation. However, use of such adapters can result in reverse transcription products that also contain complementary sequences. Such complementary sequences have the potential to generate secondary structure and, as such, can decrease the overall efficiency of the method.

A better way for decreasing bias in cDNA library preparation is therefore needed.

SUMMARY

This disclosure provides, among other things, a 5' adapter of the formula 3'*—X—(5'5')—Y—3', where: 3'* is a blocked 3' end, X is a synthetic sequence, (5'5') is an internal 5'-5' linkage, Y is an adapter sequence, and 3' is a hydroxylated 3' end. In use, sequence X hybridizes to sequence X' in a population of RNA molecules of formula R—X'. Hybridization of these sequences is believed to increase the efficiency of ligation of the 5' adapter to the nucleic acid molecules and reduce bias.

As will be described in greater detail below, in reverse transcribing the ligation products, the internal 5'-5' linkage in the adapter prevents sequence X of the adapter from being reverse transcribed, thereby eliminating a potential source of secondary structure from the reverse transcription products. Without this secondary structure, the reverse transcription products can be amplified efficiently and without significant bias.

A method for ligating the 5' adapter to RNA is provided. In some embodiments, this method may comprise: incubating a reaction mixture comprising: (i) a 5' adapter of the formula 3'*—X—(5'5')—Y—3', wherein: 3'* is a blocked 3' end, X is a synthetic sequence of at least 8 nucleotides, (5'5') is an internal 5'-5' linkage, Y is an adapter sequence of at least 8 nucleotides, and 3' is a hydroxylated 3' end; (ii) a population of nucleic acid molecules of sequence 5'-R—X'-3', wherein R is 5'-phosphorylated RNA and X' is complementary to sequence X in the 5' adapter; and (iii) a ligase capable of ligating a 5' phosphate to a 3' hydroxyl, under conditions by which sequence X of the 5' adapter hybridizes to sequence X' of the nucleic acid molecules to produce complexes and, in the complexes, the hydroxylated 3' end of the 5' adapter ligates to the 5' end of the nucleic acid molecules to produce product molecules of formula 3'*—X—(5'5')—Y—R—X'-3'.

Also provided is a 5' adapter. In some embodiments, this adapter is of the formula 3'*—X—(5'5')—Y—3', wherein: 3'* is a blocked 3' end, X is a synthetic sequence of at least 8 nucleotides, (5'5') is an internal 5'-5' linkage; Y is an adapter sequence of at least 8 nucleotides, and 3' is a hydroxylated 3' end.

A kit comprising the 5' adapter is also provided. In some embodiments, the kit may comprise a 3' adapter comprising sequence X' and/or a polymerase capable of adding a homopolymeric tail of sequence X' to an RNA.

Also provided is an oligonucleotide of the formula: 3'*—X—(5'5')—Y—Z—3', wherein: 3'* is a blocked 3' end, X is a homopolymer of at least 8 nucleotides or a synthetic sequence of at least 8 nucleotides, 5'5' is an internal 5'-5' linkage, Y is an adapter sequence of at least 8 nucleotides, Z is a random sequence of at least two nucleotides; and 3' is a hydroxylated 3' end.

BRIEF DESCRIPTION OF THE FIGURES

Some aspects of the present invention may be best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
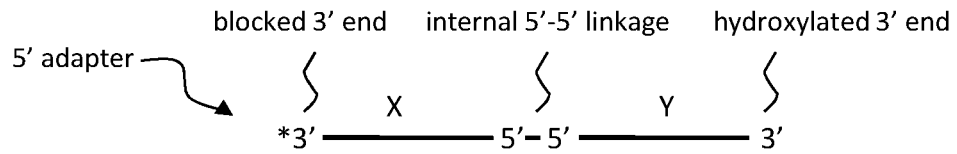
FIG. 1 schematically illustrates an embodiment of the present 5' adapter.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., *Dictionary Of Microbiology And Molecular Biology*, 2d Ed., John Wiley and Sons, New York (1994), and Hale & Markham, *The Harper Collins Dictionary Of Biology*, Harper Perennial, N.Y. (1991) provide one of skill with the general meaning of many of the terms used herein. Still, certain terms are defined below for the sake of clarity and ease of reference.

It must be noted that, as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "RNA sample", as used herein, relates to a mixture of materials, typically, although not necessarily, in liquid form, e.g., In the form of an aqueous solution, containing one or more RNA molecules. An RNA sample may be obtained from cells, e.g., mammalian cells, for example. An RNA sample may contain any number of distinguishable RNA molecules. For example, in some embodiments, an RNA sample may contain a population of different RNA molecules, in which case the RNA sample may contain more than 1,000, more than 10,000, more than 50,000, more than 100,000, or up to 1M or more different species of RNA, i.e., RNA molecules of different sequence. An RNA sample may contain long RNA molecules, such as mRNA molecules, which are typically at least 100 nucleotides (nt) in length (e.g., 200 nt to 10 kb in length) and have a median length in the range of 500-5,000 nt, as well as, for example, long intergenic noncoding RNAs (lincRNAs). An RNA sample may additionally contain a variety of small non-coding regulatory RNAs that may be generically referred herein to as "small RNAs", e.g., microRNAs, tiny non-coding RNAs, piwi-interacting small RNAs (piRNAs), small modulatory RNAs, and small nucleolar RNA (snoRNAs), etc. Small RNAs are typically below 100 nt in length and have a median length in the range of 20 nt to 40 nt. An RNA sample may additionally contain rRNA molecules, tRNA molecules, pre-miRNA molecules, and long non-coding RNA molecules such as large intergenic RNA (lincRNA) molecules. Unless otherwise indicated, an "RNA sample" may have any type of naturally-occurring RNA, including those described above and potentially others.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators). Reference to any nucleotides defined by the IUPAC code (e.g., R, Y, S, W, K, M, B, D, H, V and N includes analogs thereof that have the same base-pairing characteristics.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine, thymine and uracil (G, C, A, T and U).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In some cases, an isolated substance may be dissolved in a liquid, e.g., an aqueous liquid. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography, sedimentation according to density, precipitation, solvent extraction and solid phase purification using a column or beads. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51 to 60, 61 to 70, 71 to 80, 80 to 100, 100 to 150 or 150 to 200, up to 500 nucleotides in length, for example. The term "duplex", "hybrid" or "double-stranded" as used herein refers to nucleic acids that have two strands that are bound together by based pairing.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions.

The terms "determining", "measuring", "evaluating", "assessing", "analyzing", and "assaying" are used interchangeably herein to refer to any form of measurement or analysis and include determining if an element is present or not. These terms include both quantitative and/or qualitative determinations. Assessing may be relative or absolute. "Assessing the presence of" includes determining the amount of something present, as well as determining whether it is present or absent.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed, degraded or substantially reduced.

As used herein, the term "adapter" refers to an oligonucleotide that may be composed of any type of nucleotide. An adapter may be, e.g., an RNA adapter, a DNA adapter, or it may be composed of both ribonucleotides and deoxyribonucleotides or analogs thereof. An adapter may be of 5-50 bases, e.g., 10 to 30 bases, in length or longer depending on the application. An adapter may contain a molecular barcode, restriction sites and/or primer binding sites, depending on the application. In the methods described below, at least the 3' end of the adapter can be RNA. In some embodiments, an adapter can contain a molecular barcode (e.g., an "index" or "indexing" sequence).

As used herein, the terms "3'-OH" and "3'-hydroxyl" refer to a nucleotide at the 3' terminus of a nucleic acid, where the nucleotide has a hydroxyl group at the 3' position.

As used herein, the term "5'-P" or "5'-phosphate" refers to a nucleotide at the 5' terminus of a nucleic acid, where the nucleotide has a phosphate group at the 5' position.

As used herein, the term "cDNA library" refers to a collection of DNAs, or library, synthesized from a template RNA and are therefore complimentary to the template RNA. The cDNA library can be sequenced, labeled, amplified and/or cloned, depending on how it is going to be used.

As used herein, the term "RNA:cDNA hybrid" refers to a product after first-strand cDNA synthesis catalyzed by reverse transcriptase using RNA as a template. An "RNA-cDNA hybrid" can be full-length if the cDNA portion includes the complete sequence of the 5'-ends of the template mRNA.

As used herein, the term "template" refers to the substrate RNA for the reverse transcriptase to make cDNA. The template RNA is the target in a mixed population of RNA molecules for enrichment.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" or "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid. An internal 5'-5' linkage is a type of non-naturally occurring linkage.

In the context of a composition, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "primer" refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase or a reverse transcriptase. Primers are generally of a length compatible with their use in synthesis of primer extension products, and are usually are in the range of between 6 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Primers are usually single-stranded. Primers have a 3' hydroxyl.

The term "homopolymeric tail" refers to a sequence that with the possible exception of the last one or two nucleotides, has 3' end sequence that has a string (e.g., at least 8, at least 10 or at least 12) of the same nucleotide, e.g., a string of Ts, Us, As, Cs or Gs. This term includes anchored homopolymers, which may be of sequence $(T)_n VN$, $(U)_n VN$, $(A)_n BN$, $(C)_n DN$, or $(G)_n HN$, where n is at least 6, at least 8, at least 10, at least 12 or at least 15, and T, U, A and C are thymine, uracil, adenine and cytosine nucleotides, or analogs thereof that are capable of base paring in the same way.

The term "oligo-dT primer" refers to a primer that is capable of priming cDNA synthesis from a polyA tail. With the possible exception of the last one or two nucleotides, an oligo-dT primer may have a 3' end sequence that has a string of thymines. Such a primer may have a 5' tail. In some embodiments, oligo-dT primer may be anchored and may have the following sequence: TTTTTTTTTTTTTTTVN (SEQ ID NO:1), where V is G, A or C or analog thereof and N is any nucleotide or analog thereof. The T in such an oligonucleotide may be a T analog in that it is capable of specifically base pairing with an A.

The term "sequence-specific primer" for the purpose of reverse transcribing an RNA is intended to refer to a primer that hybridizes to a unique sequence in an RNA, e.g., an mRNA. Sequence-specific primers do not have a random sequence and are not made of a single nucleotide. Random primers and oligo(T) primers are not sequence specific primers.

The term "cDNA copy" refers to a DNA molecule that has the reverse complement of an RNA molecule (i.e., first strand cDNA) or a DNA molecule that has the same sequence as an RNA molecule except that the Us are T's (i.e., second strand cDNA).

Certain polynucleotides described herein may be referred by a formula (e.g., "3'*—X—(5'5')—Y—3'"). Unless otherwise indicated, the polynucleotides defined by a formula (as in the case for 3'*—X—(5'5')—Y—3') are oriented in the 5' to 3' direction. The components of the formula, e.g., "X" and "Y" etc., refer to separately definable sequences of nucleotides within a polynucleotide, where, unless implicit from the context the sequences are linked together covalently such that a polynucleotide described by a formula is a single molecule. Following convention, the complement of a sequence shown in a formula will be indicated with a prime (') such that the complement of sequence "X" will be "X'". Moreover, unless otherwise indicated or implicit from the context, a polynucleotide defined by a formula may have additional sequence, a primer binding site, a molecular barcode, a promoter, or a spacer, etc., at its 3' end, its 5' end or both the 3' and 5' ends. In many cases the components of the formula are immediately adjacent to one another in the single molecule. In many cases there may one or more other sequences between the recited components. As would be apparent, the various component sequences of a polynucleotide (e.g., X, Y, R, W, etc.) may independently be of any desired length so long as they capable of performing the desired function (e.g., hybridizing to another sequence). For example, the various component sequences of a polynucleotide may independently have a length in the range of 8-80 nucleotides, e.g., 10-50 nucleotides. As would be apparent, an adapter, primer or product having a particular formula is made up of a population of adapters, primers, or product molecules that are described by the formula. If, for example, a sequence is "random" or "variable" in a population, then that sequence is represented by several different sequences in the population.

The term "internal 5'-5' linkage" refers to a linkage in which the 5th position of the sugar of a first nucleotide is covalently linked, directly or indirectly (e.g., via a phosphate or another type of linkage), to the 5th position of the sugar of a second nucleotide.

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods

Figure 2:
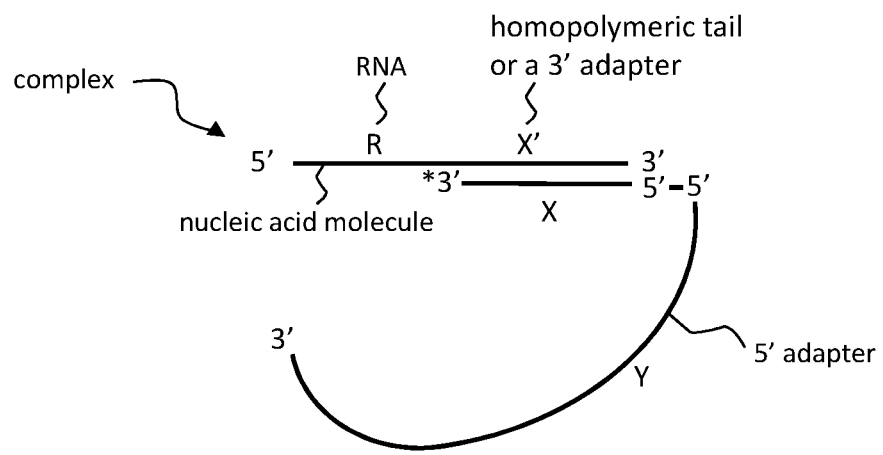
FIG. 2 schematically illustrates a complex formed by hybridization of the 5' adapter illustrated in FIG. 1 and a nucleic acid molecule of formula R—X'.
Figure 3:
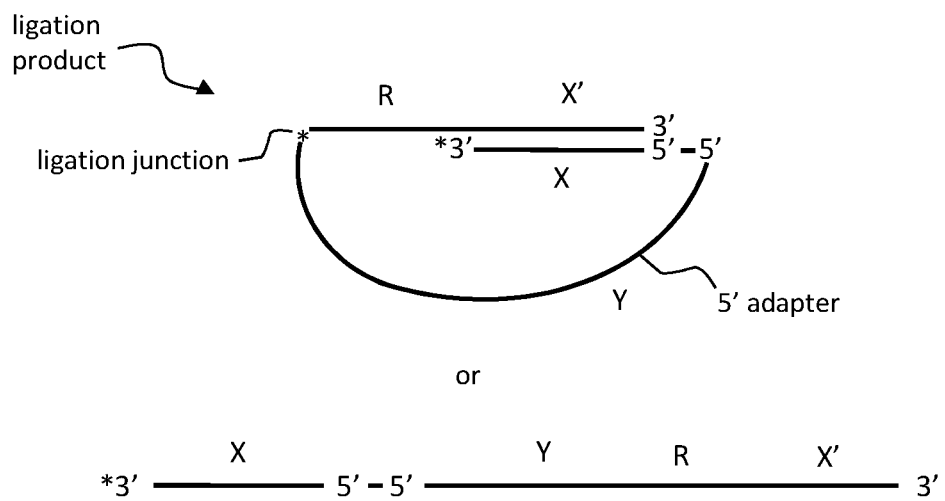
FIG. 3 schematically illustrates how the method can be used to produce a ligation product of formula *3'—X—(5'-5')—Y—R—X'-3'.

FIGS. 1-3 show an example of a method for ligating a 5' adapter to RNA is provided. In some embodiments, the method may comprise incubating a reaction mixture comprising: a 5' adapter; a population of nucleic acid molecules; and a ligase under conditions by which the 3' end of the 5' adapter ligates to the 5' end of the nucleic acid molecules. As illustrated in FIG. 1, the adapter is of the formula 3'*—X—(5'5')—Y—3', where 3'* is a blocked 3' end, X is a synthetic sequence of at least 8 nucleotides, (5'5') is an internal 5'-5' linkage, Y is an adapter sequence of at least 8 nucleotides, and 3' is a hydroxylated 3' end. Sequences X and Y may independently be at least 8, at least 10, at least 12, or at least 15 nucleotides in length. The sequence and functions of sequences X and Y will be described in greater detail below. The blocked 3' is not ligatable and, as such, does not contain a 3' hydroxyl. As shown in FIG. 1, the 5' adapter is effectively composed of two sequences X and Y that are joined by their 5' ends via an internal 5' to 5' linkage such that the adapter has two 3' ends. As shown, one of the 3' ends is blocked in that it does not have a 3' hydroxyl and cannot be ligated to the 5' phosphate. The 5' adapter may be a single-stranded oligonucleotide in the range of 16 nt in length (e.g., at least 20 or at least 25 nt in length), although adapters having a length outside of this range may also be employed. In some embodiments, the 5' adapter may be of the formula 3'*—X—(5'5')—Y—Z—3', where X and Y are summarized above, and Z is a random sequence of at least two (e.g., 2, 3, or 4 or more) nucleotides (see, e.g., Fuchs et al, PLoS ONE 10: e0126049. and US20170137875, for example). The random sequence at the 3' end of the 5' adapter may help reduce bias in addition to sequence X in the 5' adapter.

The population of nucleic acid molecules is illustrated in FIG. 2. As shown, the population of nucleic acid molecules is of the formula 5'-R—X'-3', wherein R is a 5'-phosphorylated RNA and X' is complementary to sequence X in the 5' adapter. As shown, sequence X' may be a homopolymeric tail that has been added onto the RNA (e.g., a polyA tail added onto the RNA in a cell, or a poly(A), poly(G) or poly(U) tail added onto the RNA in vitro by a poly(A), poly(G) or poly(U) polymerase), or a 3' adapter that has been ligated to the RNA. As would be apparent, the ligase used in the method should be capable of ligating a 5' phosphate to a 3' hydroxyl. The 5' adapter may be an RNA oligonucleotide, a DNA oligonucleotide or an oligonucleotide that comprises DNA and RNA. The 5' adapter may be ligated onto the RNA molecules of the digested sample using an RNA ligase, e.g., T4 RNA ligase, using any of the methods outlined in Wang et al (RNA 2007 13: 151-159) or Lockhart et al (U.S. Pat. No. 6,344,316), among many others. The RNA ligase used in the method can be any suitable ligase. In some embodiments, T4 RNA ligase can be used, although a variety of other RNA ligases that have a preference for single-stranded substrates can be used instead. In some embodiments, the RNA ligase used may be thermostable. In these embodiments, the ligation reaction may be performed at an elevated temperature that may be in the range of 40° C. to 80° C. The ligation is performed under conditions by which sequence X of the 5' adapter hybridizes to sequence X' of the nucleic acid molecules to produce complexes and, in the complexes, the hydroxylated 3' end of the 5' adapter ligates to the 5' end of the nucleic acid molecules to produce product molecules of formula 3'*—X—(5'5')—Y—R—X'-3'. An exemplary complex is illustrated in FIG. 2. As shown in FIG. 2, in the complex, sequence X of the 5' adapter hybridizes to the complementary sequence in the nucleic acid molecules (i.e., X') to produce a complex in which the 3' end of the 5' adapter is proximal to the 3' end of the nucleic acid molecules, thereby facilitating the ligation of those ends in a way that reduces sequence bias. FIG. 3 illustrates the product molecules of formula 3'*—X—(5'5')—Y—R—X'-3', with (top) and without (bottom) the secondary structure generated by hybridization of X to X'.

As noted above, sequence X in the adapter and complementary sequence X' in the nucleic acid molecule can vary depending on how the method is implemented. As noted above, sequence X' can be, e.g., a natural poly(A) tail (i.e., a poly(A) tail added to RNA in the cell from which the RNA is obtained). In these embodiments, the nucleic acid molecules may be poly(A)$^+$ RNA (e.g., mRNA isolated from a eukaryotic cell), where X' is the poly(A) tail and R is the sequence of nucleotides that is 5' to the poly(A) tail. In these embodiments, X in the adapter may comprise a homopolymer of T (or another nucleotide that can base pair with A, such as U) which is complementary to and can hybridize to the poly(A). In other embodiments, sequence X' in the nucleic acid molecules can be added to the 3' end of the RNA by a polymerase in vitro. This reaction can be performed by a poly(A), poly(G) or poly(U) polymerase and so, in some embodiments, sequence X' in the nucleic acid molecules may be poly(A), poly(G) or poly(U), for example. In these embodiments, the nucleic acid molecules may comprise RNA of sequence R and a homopolymeric tail that has been added onto the RNA. In other embodiments, sequence X in the nucleic acid molecules can be added to the 3' end of the RNA by ligating a 3' adapter onto the end of the RNA. In these embodiments, sequence X' in the nucleic acid molecules is a 3' adapter that has been ligated onto the 3' end of the RNA. As would be apparent, in these embodiments, the sequence of X does not need to be a homopolymer and in certain cases may be in the range of 8-20 nucleotides in length that is not complementary to other sequences in the sample. 3' adapters are conventional in library construction. If the present method is implemented using a 3' adapter, then the 5' adapter can be designed to have a sequence that is complementary to a sequence in the 3' adapter.

If the method comprises adding an adapter or homopolymeric tail onto the 3' end of the RNA, then the RNA may be, e.g., small RNA, prokaryotic RNA, fragmented mRNA, or fragments of prokaryotic RNA).

Figure 4:
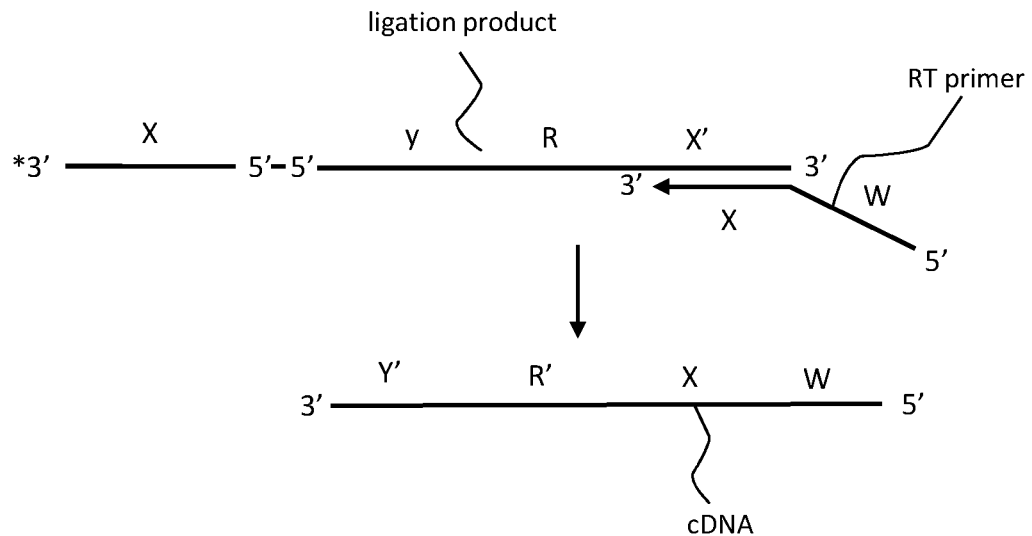
FIG. 4 schematically illustrates how the ligation product shown in FIG. 3 can be reverse transcribed.
Figure 5:
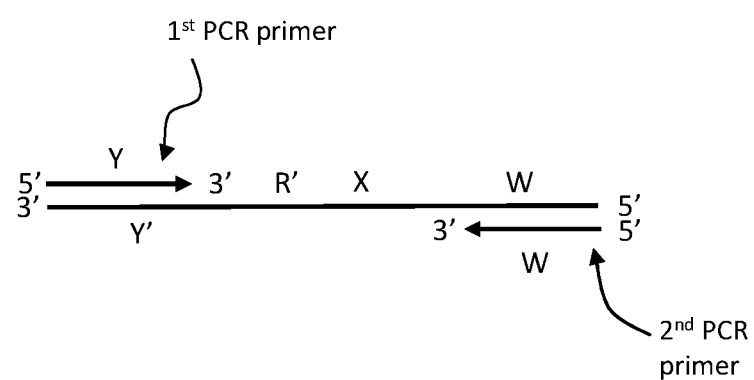
FIG. 5 schematically illustrates how the reverse transcription product shown in FIG. 4 can be amplified. One or both of the PCR primers may have a 5' tail.

In some embodiments, the method may further comprise reverse transcribing the ligation products to produce cDNA, and then amplifying the cDNA. These steps are illustrated in FIGS. 4 and 5. With reference to FIG. 4, some embodiments of the method may comprise hybridizing a reverse transcription primer to sequence X' of the ligation product. As shown, the reverse transcription primer should have a sequence at its 3' end that is complementary to X' in the ligation product. If X' is a homopolymer, the 3' end of the reverse transcription primer should comprise a complementary homopolymer. In some embodiments, reverse transcription primer may comprise an anchored homopolymer at the 3' end, which may be of sequence $(T)_n VN$, $(U)_n VN$, $(A)_n BN$, $(C)_n DN$, or $(G)_n HN$, where n is at least 8, at least 10, at least 12 or at least 15. As would be apparent, if X' is a sequence in a 3' adapter, the 3' end of the reverse transcription primer should hybridize to that sequence. In some embodiments and as shown in FIG. 4, the reverse transcription primer may contain a 5' tail of sequence W, which does not hybridize the same target as the 3' end of the primer and may have a length in the range of 12-50 nucleotides. Reverse transcription of the ligation product produces a cDNA of formula 3'—Y'—R'—X—5'. If the reverse transcription primer has a 5' tail of sequence W, then the cDNA is of formula 3'—Y'—R'—X—W—5'. As noted above, the internal 5'-5' linkage blocks reverse transcription of sequence X of the ligation products and, as such, the cDNA produced by the method does not contain sequence X' at its 3' end. Rather, reverse transcription is terminated across from the 5'-5' linkage, to produce a cDNA of formula 3'—Y'—R'—X—W—5'.

FIG. 5 shows how a cDNA of formula 3'—Y'—R'—X—W—5' can be amplified by a pair of primers which may comprise a first PCR primer that hybridizes to sequence Y' in the cDNA and a second PCR primer that has sequence W. One or both of these primers may comprise a 5' tail, if desired. In some embodiments, the primers used may have sequences that are compatible with the sequencing platform being used (e.g., P5 and P7 sequences, which sequences are compatible with Illumina's sequencing platform) and the amplification products will have those sequences at their ends (e.g., P5 sequence at one and the P7 sequence at the other, if the Illumina sequencing platform is being used).

In some embodiments, the population of nucleic acid molecules of is made by: i. exposing an RNA sample comprising RNA to fragmentation conditions to produce RNA fragments; and ii. adding sequence X' onto the 3' end of the RNA fragments, e.g., by ligation or using a poly(A), poly(G) or poly(U) polymerase, as discussed above. The RNA in the RNA sample may be fragmented in a variety of different ways. For example, the RNA sample may contain cDNA:RNA hybrids (i.e., may comprise reverse transcription products primed using, e.g., an oligo(dT) primer), and the fragmenting of the RNA may be performed by treating the sample with RNAseH (see U.S. application Ser. No. 15/818,469, filed on Nov. 20, 2017, which is incorporated by reference herein). Fragmentation can also be performed by hybridizing a random DNA oligonucleotide to the RNA to produce cDNA:RNA hybrids and then treating the hybrids with RNase H. Alternatively, the RNA may be fragmented by heating the mRNA (e.g., to a temperature of at least 60° C.) for a period of at least 5 minutes in the presence of a divalent cation (e.g., $Mg^{2+}$ or $Zn^{2+}$)) or another method (see, for example, Leven et al Nat Methods. 2010 7: 709-715). Some of the alternative methods produce RNA fragments that have 5' hydroxyl and a 3' phosphate and, as such, may require a phosphatase and/or kinase treatment before moving on to the next step.

In some embodiments, the initial sample (prior to fragmentation) may comprise small RNAs that are in the range 20 and 50 nucleotides in length and have a median length in the range of 20 nt to 40 nt, in addition to longer RNA (mRNA and lncRNA). Small RNAs include microRNA (miRNA) molecules, tiny non-coding RNA (tncRNA) molecules and small modulatory RNA (smRNA) molecules, as well as others. In these embodiments, the initial fragmentation step may avoid fragmenting the small RNAs. For example, if the initial RNA is fragmented by heat in the presence of a divalent cation (which primarily cleaves long RNAs such as mRNAs because they contain more cleavage sites than short RNAs), then the cleavage reaction can be terminated before the small RNAs are significantly fragmented. In other embodiments, RNase H can be used. If small RNAs are present in the sample, then the mRNAs may be fragmented to a median length that is similar to the length of the small RNAs. Small RNAs can be in the range of 20-29 nucleotides in length, and many small RNAs are approximately 20-29 nucleotides in length. As such, if small RNAs and longer RNAs such as mRNAs are going to be analyzed, then the longer RNAs may be fragmented to a median length of between 20 to 100 nucleotides, e.g., 25 to 50 nucleotides. As such, in some embodiments, the method may comprise fragmenting the sample to produce a RNA product, where the RNA product comprises small RNAs and fragments of the longer RNA. In these embodiments, both the small RNAs and the RNA fragments have a 5' phosphate and a 3' hydroxyl and, as such, can be ligated to the 5' adapter using the method described above. The resultant cDNA library may contain cDNA copies of the mRNA fragments as well as cDNA copies of the small RNA. These molecules can be amplified and analyzed together and so this embodiment of the method provides a way to analyze small RNAs and longer RNAs, e.g., mRNA, in the same workflow. In these embodiments, the population of nucleic acid molecules of may comprise: i. small RNAs and RNA fragments and ii. sequence X', wherein the cDNA comprises cDNA copies of the small RNAs and cDNA copies of the RNA fragments.

In embodiments in which the cDNAs are sequenced, the cDNA library may be amplified using one or more primers that hybridize to the added sequences (or their complements), as described above. The sequencing step may be done using any convenient next generation sequencing method and may result in at least 10,000, at least 50,000, at least 100,000, at least 500,000, at least 1M, at least 10M, at least 100M, at least 1B, or at least 10B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

In certain embodiments, the cDNA that is sequenced may comprise a pool of cDNA libraries made from a plurality of different RNA samples, wherein the different cDNA libraries have a molecular barcode (in the adapter or PCR primers) to indicate their source. In some embodiments, the cDNAs being analyzed may be derived from a single source (e.g., a single organism, virus, tissue, cell, subject, etc.), whereas in other embodiments, the cDNAs that are sequenced may be a pool of nucleic acids extracted from a plurality of sources (e.g., a pool of nucleic acids from a plurality of organisms, tissues, cells, subjects, etc.), where by "plurality" is meant as two or more. As such, in certain embodiments, cDNAs that are sequenced can contain nucleic acids from 2 or more sources, 3 or more sources, 5 or more sources, 10 or more sources, 50 or more sources, 100 or more sources, 500 or more sources, 1000 or more sources, 5000 or more sources, and up to and including about 10,000 or more sources. Molecular barcodes may allow the sequences from different sources to be distinguished after they are analyzed. The sequence reads may be analyzed by a computer and, as such, instructions for performing the steps set forth below may be set forth as programing that may be recorded in a suitable physical computer readable storage medium.

Compositions

Also provided are a variety of compositions. In some embodiments, a composition may comprise a 5' adapter of the formula 3'*—X—(5'5')—Y—3', wherein 3'* is a blocked 3' end, X is a synthetic sequence of at least 8 nucleotides, (5'5') is an internal 5'-5' linkage; Y is an adapter sequence of at least 8 nucleotides, and 3' is a hydroxylated 3' end, as described above. In some embodiments, sequence X is complementary to a homopolymeric tail of sequence X' or to a 3' adapter comprising sequence X'. In particular cases, sequence X may an anchored homopolymer of sequence $(T)_nVN$, $(U)_nVN$, $(A)_nBN$, $(C)_nDN$, or $(G)_nHN$, for example, where V is A, C, G (not T), B is C, G, T (not A), D is A, G, T (not C), and H is A, C, T (not G), or an analog thereof that base pairs in the same way. In some embodiments, a composition may comprise an oligonucleotide of the formula: 3'*—X—(5'5')—Y—Z—3', wherein: 3'* is a blocked 3' end, X is a homopolymer of at least 8 nucleotides or a synthetic sequence of at least 8 nucleotides; 5'5' is an internal 5'-5' linkage; Y is an adapter sequence of at least 8 nucleotides; Z is a random sequence of at least two nucleotides; and 3' is a hydroxylated 3' end.

Kits

Also provided by this disclosure are kits for practicing the subject methods. The kits may comprise any of the components described above. For example, in some embodiments, a kit may comprise a 5' adapter 5' adapter of the formula 3'*—X—(5'5')—Y—3', wherein 3'* is a blocked 3' end, X is a synthetic sequence of at least 8 nucleotides, (5'5') is an internal 5'-5' linkage; Y is an adapter sequence of at least 8 nucleotides, and 3' is a hydroxylated 3' end, as described above. In some embodiments, the adapter may be of the formula: 3'*—X—(5'5')—Y—Z—3', wherein: 3'* is a blocked 3' end, X is a homopolymer of at least 8 nucleotides or a synthetic sequence of at least 8 nucleotides; 5'5' is an internal 5'-5' linkage; Y is an adapter sequence of at least 8 nucleotides; and Z is a random sequence of at least two nucleotides, as described above. In some embodiments, the kit may additionally comprise a 3' adapter comprising sequence X', and/or a polymerase capable of adding a homopolymeric tail of sequence X' to an RNA (e.g., a poly(A), poly(G) or poly(U) polymerase). In some embodiments, a kit may additionally comprise a reverse transcription primer that has a 3' sequence that is complementary to and thereby hybridizes to sequence X' and, optionally, a 5' tail comprising sequence W. In these embodiments, the 3' sequence that hybridizes to sequence X' hybridizes to poly (A), poly(G), or poly(U). In some embodiments, the reverse transcription primer may have a 3' sequence of sequence $(T)_nVN$, $(U)_nVN$, $(A)_nBN$, $(C)_nDN$, or $(G)_nHN$. In addition, in some embodiments, the kit may further comprise at least two PCR primers, comprising: (i) a first PCR primer, having a 3' sequence that is complementary to the cDNA copy of sequence Y of the 5' adapter; and (ii) a second PCR primer having a 3' end of sequence W. A kit may additionally comprise reverse transcriptase, ligase, dNTPs, and/or poly (A) polymerase, as well as any necessary buffers (typically in concentrated form).

The various components of the kit may be present in separate containers or certain compatible components may be precombined into a single container, as desired.

In addition to the above-mentioned components, the subject kit may further include instructions for using the components of the kit to practice the subject method.

Utility

The method described herein can be employed to analyze RNA (e.g., mRNA and, optionally, small RNAs) from virtually any organism and/or sample-type, including, but not limited to, plants, animals (e.g., reptiles, mammals, insects, worms, fish, etc.), tissue samples, cadaveric tissue, archaeological/ancient samples, etc. In certain embodiments, the RNA sample used in the method may be derived from a mammal, where in certain embodiments, the mammal is a human. In exemplary embodiments, the RNA sample may contain RNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the RNA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cfRNA obtained from blood, e.g., from the blood of a pregnant female or a patient.

The present method may be employed in a variety of diagnostic, drug discovery, and research applications that include, but are not limited to, diagnosis or monitoring of a disease or condition (where the expression of an mRNA and/or small RNA provides a marker for the disease or condition), discovery of drug targets (where an mRNA and/or small RNA is differentially expressed in a disease or condition and may be targeted for drug therapy), drug screening (where the effects of a drug are monitored by assessing the level of an mRNA and/or small RNA), determining drug susceptibility (where drug susceptibility is associated with a particular profile of an mRNA and/or small RNA), and basic research (where is it desirable to identify the presence of an mRNA and/or small RNA in a sample, or, in certain embodiments, the relative levels of a particular mRNA and/or small RNA in two or more samples).

In certain embodiments, relative levels of an mRNA and/or small RNA in two or more different small RNA samples may be obtained using the above method and compared. In these embodiments, the results obtained from the above-described methods are usually normalized to the total amount of RNA in the sample or to control RNAs (e.g., constitutive RNAs), and are compared. This may be done by comparing ratios, or by any other means. In particular embodiments, the mRNA and/or small RNA profiles of two or more different samples may be compared to identify mRNAs and/or small RNAs that are associated with a particular disease or condition (e.g., an mRNA and/or small RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., a normal cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

In some embodiments, the sequence reads may be analyzed to provide a quantitative determination of which sequences are in the sample. This may be done by, e.g., counting sequence reads or, alternatively, counting the number of original starting molecules, prior to amplification, based on their fragmentation breakpoint and/or whether they contain the same indexer sequence (which can be present in the 5' adapter, for example). The use of molecular barcodes in conjunction with other features of the fragments (e.g., the end sequences of the fragments, which define the breakpoints) to distinguish between the fragments is known. Molecular barcodes and exemplary methods for counting individual molecules are described in Casbon (Nucl. Acids Res. 2011, 22 e81) and Fu et al (Proc Natl Acad Sci USA. 2011 108: 9026-31), among others. Molecular barcodes are described in U.S. 2015/0044687, U.S. 2015/0024950, U.S. 2014/0227705, U.S. Pat. Nos. 8,835,358 and 7,537,897, as well as a variety of other publications.

Also provided is a method for identifying a pattern that correlates with phenotype, e.g., a disease, condition or clinical outcome, etc. In some embodiments, this method may comprise: (a) performing the above-described method on a plurality of RNA samples, wherein the RNA samples are isolated from patients having a known phenotype, e.g., disease, condition or clinical outcome, thereby determining which RNAs from each of the patients; and (b) identifying a signature that is correlated with the phenotype.

In some embodiments, the signature may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

Also provided is a method for analyzing a patient sample. In this embodiment, the method may comprise: (a) identifying, using the above-described method, sequences that are under and/or over expressed in a patient; (b) comparing the identified sequences to a set of signature sequences that are correlated with a phenotype, e.g., a disease, condition, or clinical outcome etc.; and (c) providing a report indication a correlation with phenotype. This embodiment may further comprise making a diagnosis, prognosis, or theranosis based on the results of the comparison.

In some embodiments, the method may involve creating a report as described above (an electronic form of which may have been forwarded from a remote location) and forwarding the report to a doctor or other medical professional to determine whether a patient has a phenotype (e.g., cancer, etc.) or to identify a suitable therapy for the patient. The report may be used as a diagnostic to determine whether the subject has a disease or condition, e.g., a cancer. In certain embodiments, the method may be used to determine the stage or type cancer, to identify metastasized cells, or to monitor a patient's response to a treatment, for example.

In any embodiment, a report can be forwarded to a "remote location", where "remote location," means a location other than the location at which an image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible), and includes, at least in the case of data, physically transporting a medium carrying the data or communicating the data. Examples of communicating media include radio or infra-red transmission channels, as well as a network connection to another computer or networked device, and the internet or including email transmissions and information recorded on websites and the like. In certain embodiments, the report may be analyzed by an MD or other qualified medical professional, and a report based on the results of the analysis of the image may be forwarded to the patient from which the sample was obtained.

Accordingly, among other things, the instant methods may be used to link the expression of certain genes to certain physiological events.

EMBODIMENTS

Embodiment 1. A method for ligating a 5' adapter to RNA, comprising: incubating a reaction mixture comprising:
(i) a 5' adapter of the formula

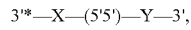

wherein: 3'* is a blocked 3' end, X is a synthetic sequence of at least 8 nucleotides, (5'5') is an internal 5'-5' linkage, Y is an adapter sequence of at least 8 nucleotides, and 3' is a hydroxylated 3' end;
(ii) a population of nucleic acid molecules of the formula 5'-R—X'-3', wherein R is 5'-phosphorylated RNA and X' is complementary to sequence X in the 5' adapter; and
(iii) a ligase capable of ligating a 5' phosphate to a 3' hydroxyl,
under conditions by which sequence X of the 5' adapter hybridizes to sequence X' of the nucleic acid molecules to produce complexes and, in the complexes, the hydroxylated 3' end of the 5' adapter ligates to the 5' end of the nucleic acid molecules to produce product molecules of formula 3'*—X—(5'5')—Y—R—X'-3'.

Embodiment 2. The method of embodiment 1, wherein sequence X' in the nucleic acid molecules is a homopolymeric tail.

Embodiment 3. The method of embodiment 1, wherein sequence X' in the nucleic acid molecules is a 3' adapter that has been ligated to the RNA.

Embodiment 4. The method of any prior embodiment, wherein the population of nucleic acid molecules of (ii) is made by: i. exposing an RNA sample to fragmentation conditions to produce RNA fragments; and ii. adding sequence X' onto the 3' end of the RNA fragments.

Embodiment 5. The method of any prior embodiment, further comprising: reverse transcribing the product molecules to produce cDNA of formula 3'—Y'—R'—X'—5', wherein the internal 5'-5' linkage blocks reverse transcription of sequence X of the product molecules.

Embodiment 6. The method of any prior embodiment, wherein the population of nucleic acid molecules of (ii) comprises: i. small RNAs and RNA fragments; and ii. sequence X', wherein the cDNA comprises cDNA copies of the small RNAs and cDNA copies of the RNA fragments.

Embodiment 7. The method of embodiments 5 or 6, further comprising amplifying the cDNA.

Embodiment 8. The method of any of embodiments 5-7, further comprising sequencing the cDNA, or an amplification product thereof.

Embodiment 9. The method of any prior embodiment, wherein the 5' adapter of (i) is of the formula

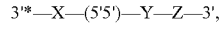

wherein Z is a random sequence of at least two nucleotides.

Embodiment 10. A 5' adapter of the formula

3'*—X—(5'5')—Y—3', wherein: 3'* is a blocked 3' end, X is a synthetic sequence of at least 8 nucleotides, (5'5') is an internal 5'-5' linkage; Y is an adapter sequence of at least 8 nucleotides, and 3' is a hydroxylated 3' end.

Embodiment 11. The 5' adapter of embodiment 10, wherein X is complementary to a homopolymeric tail of sequence X' or to a 3' adapter comprising sequence X'.

Embodiment 12. The 5' adapter of embodiment 10 or 11, wherein X is an anchored homopolymer of sequence $(T)_nVN$, $(U)_nVN$, $(A)_nBN$, $(C)_nDN$, or $(G)_nHN$.

Embodiment 13. A kit comprising a 5' adapter of any of embodiments 10-12.

Embodiment 14. The kit of embodiment 13, further comprising a 3' adapter comprising sequence X'.

Embodiment 15. The kit of embodiments 13 or 14, further comprising a polymerase capable of adding a homopolymeric tail of sequence X' to an RNA.

Embodiment 16. The kit of any of embodiments 13-15, further comprising a reverse transcription primer that has a 3' sequence that hybridizes to sequence X' and, optionally, a 5' tail comprising sequence W.

Embodiment 17. The kit of embodiment 16, wherein the 3' sequence that hybridizes to sequence X' hybridizes to poly(A), poly(G), or poly(U).

Embodiment 18. The kit of any embodiments of 13-17, wherein the reverse transcription primer has a 3' sequence of sequence $(T)_nVN$, $(U)_nVN$, $(A)_nBN$, $(C)_nDN$, or $(G)_nHN$.

Embodiment 19. The kit of any of embodiments 13-18, further comprising at least two PCR primers, comprising: (i) a first PCR primer, having a 3' sequence that is complementary to the cDNA copy of sequence Y of the 5' adapter; and (ii) a second PCR primer having a 3' end of sequence W.

Embodiment 20. The kit of any of embodiments 13-19, wherein the 5' adapter is of the formula

3'*—X—(5'5')—Y—Z—3', wherein Z is a random sequence of at least two nucleotides.

Embodiment 21. An oligonucleotide of the formula:

3'*—X—(5'5')—Y—Z—3', wherein:
3'* is a blocked 3' end,
X is a homopolymer of at least 8 nucleotides or a synthetic sequence of at least 8 nucleotides;
5'5' is an internal 5'-5' linkage;
Y is an adapter sequence of at least 8 nucleotides;
Z is a random sequence of at least two nucleotides; and
3' is a hydroxylated 3' end.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

1 ng of Miltenyi miRXplore Universal Reference (130-094-407), which is a pool of 963 equimolarly mixed miRNAs, was polyadenylated, ligated to adapters, reverse transcribed and amplified essentially as described in U.S. patent application Ser. No. 15/818,469, filed on Nov. 20, 2017 (which is incorporated by reference herein) using the 5' adapters shown below:

```
Standard 5'4N
                                        (SEQ ID NO: 2)
5'rGrUrUrCrArGrArGrUrUrCrUrArCrArGrUrCrCrGrArCrGr
ArUrCrNrNrNrN3'

5'4N_6TVN
                                        (SEQ ID NO: 3)
3'ddNVTTTTTT5'-5'rGrUrUrCrArGrArGrUrUrCrUrArCrArGr
UrCrCrGrArCrGrArUrCrNrNrNrN3'

5'4N_10TVN
                                        (SEQ ID NO: 4)
3'ddNVTTTTTTTTTT5'-5'rGrUrUrCrArGrArGrUrUrCrUrArCr
ArGrUrCrCrGrArCrGrArUrCrNrNrNrN3'
```

Each adapter was diluted to 2.5 uM before use.

Libraries were sequenced on an Illumina MiSeq. Fastq files were generated and reads were trimmed using cutadapt then aligned to a reference consisting of the 963 synthetic miRNAs in the miRXplore pool using bowtie2. All sequencing libraries were subsampled to 60,589 reads. Samtools idxstats was used to generate read counts aligning to each reference miRNA. The results of this experiment are shown in FIG. 6.

In this experiment, bias can be measured by observing the number and extent of over- and under-represented miRNAs in this equimolar pool.

Figure 6:
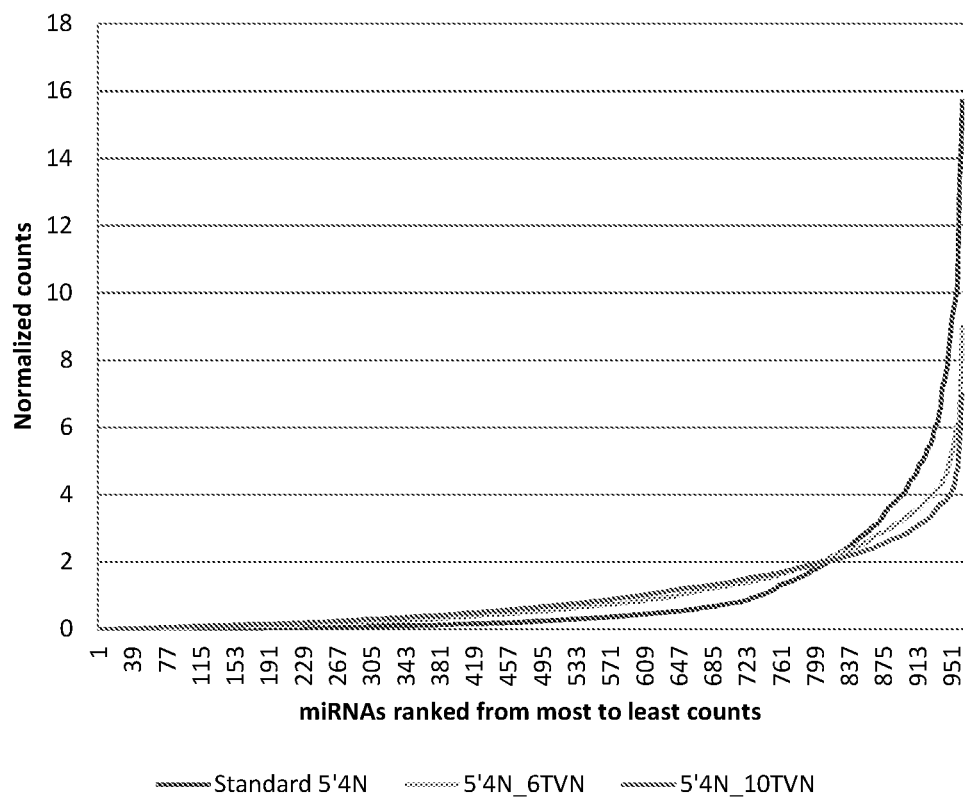
FIG. 6 is a graph showing the results of an experiment described in the examples.

FIG. 6 shows that the standard 5'4N adapter (which does not contain an inverted linkage or an oligo-dT region) produces more bias than the other adapters, and that the least bias is generated by the adapter that contains an inverted linkage and a longer oligo-dT region.

That which is claimed is:

1. A 5' adapter of the formula

3'*—X—(5'5')—Y—3', wherein: 3'* is a blocked 3' end, X is a sequence of at least 8 nucleotides, (5'5') is an internal 5'-5' linkage; Y is an adapter sequence of at least 8 nucleotides, X and Y are not complementary, and 3' is a hydroxylated 3' end.

2. The 5' adapter of claim 1,
   wherein: (i) X is complementary to sequence X', and wherein X' comprises a homopolymeric sequence, or
   (ii) X is complementary to sequence X', and wherein X' is comprised within a 3' adapter.

3. The 5' adapter of claim 1, wherein X is an anchored homopolymer of sequence $(T)_n VN$, $(U)_n VN$, $(A)_n BN$, $(C)_n DN$, or $(G)_n HN$, wherein n is at least 6.

4. A kit comprising a 5' adapter of claim 1 provided in a container.

5. The kit of claim 4, further comprising a 3' adapter comprising sequence X'.

6. The kit of claim 4, further comprising a polymerase capable of adding sequence X' to an RNA, wherein sequence X' is a homopolymeric tail.

7. The kit of claim 4, further comprising a reverse transcription primer that has a 3' sequence and optionally, a 5' tail, and wherein the 3' sequence hybridizes to sequence X'.

8. The kit of claim 7, wherein the 3' sequence that hybridizes to sequence X' hybridizes to poly(A), poly(G), or poly(U).

9. The kit of claim 7, wherein the reverse transcription primer has a 3' sequence of sequence $(T)_n VN$, $(U)_n VN$, $(A)_n BN$, $(C)_n DN$, or $(G)_n HN$, wherein n is at least 6.

10. The kit of claim 4, further comprising at least two PCR primers, comprising: (i) a first PCR primer, having a 3' sequence that is complementary to the cDNA copy of sequence Y of the 5' adapter; and (ii) a second PCR primer.

11. The kit of claim 4, wherein the 5' adapter is of the formula

3'*—X—(5'5')—Y—Z—3', wherein Z is a random sequence of at least two nucleotides.

12. An oligonucleotide of the formula:

3'*—X—(5'5')—Y—Z—3', wherein:
    3'* is a blocked 3' end,
    X is a homopolymer of at least 8 nucleotides or a sequence of at least 8 nucleotides;
    5'5' is an internal 5'-5' linkage;
    Y is an adapter sequence of at least 8 nucleotides;
    Z is a random sequence of at least two nucleotides;
    X and Y are not complementary; and
    3' is a hydroxylated 3' end.

13. A method for ligating a 5' adapter to RNA, comprising:
    incubating a reaction mixture comprising:
    (i) a 5' adapter of the formula

3'*—X—(5'5')—Y—3', wherein: 3'* is a blocked 3' end, X is a sequence of at least 8 nucleotides, (5'5') is an internal 5'-5' linkage, Y is an adapter sequence of at least 8 nucleotides, X and Y are not complementary, and 3' is a hydroxylated 3' end;
    (ii) a population of nucleic acid molecules of the formula 5'-R—X'-3', wherein R is 5'-phosphorylated RNA and X' is complementary to sequence X in the 5' adapter; and
    (iii) a ligase capable of ligating a 5' phosphate to a 3' hydroxyl,
    under conditions by which sequence X of the 5' adapter hybridizes to sequence X' of the nucleic acid molecules to produce complexes and, in the complexes, the hydroxylated 3' end of the 5' adapter ligates to the 5' end of the nucleic acid molecules to produce product molecules of formula 3'*—X—(5'5')—Y—R—X'-3'.

14. The method of claim 13, wherein sequence X' in the nucleic acid molecules is a homopolymeric tail.

15. The method of claim 13, wherein sequence X' in the nucleic acid molecules is a 3' adapter that has been ligated to the RNA.

16. The method of claim 13, wherein the population of nucleic acid molecules of (ii) is made by: i. exposing an RNA sample to fragmentation conditions to produce RNA fragments; and ii. adding sequence X' onto the 3' end of the RNA fragments.

17. The method of claim 13, further comprising:
    reverse transcribing the product molecules to produce cDNA of formula 3'—Y'—R'—X—5', wherein the internal 5'-5' linkage blocks reverse transcription of sequence X of the product molecules.

18. The method of claim 13, wherein the population of nucleic acid molecules of (ii) comprises: i. small RNAs and RNA fragments; and ii. sequence X', wherein the cDNA comprises cDNA copies of the small RNAs and cDNA copies of the RNA fragments.

19. The method of claim 17, further comprising amplifying the cDNA.

20. The method of claim 17, further comprising sequencing the cDNA, or an amplification product thereof.

21. The method of claim 13, wherein the 5' adapter of (i) is of the formula

3'*—X—(5'5')—Y—Z—3', wherein Z is a random sequence of at least two nucleotides.

* * * * *